United States Patent [19]

Trachtman

[11] Patent Number: 5,374,193
[45] Date of Patent: Dec. 20, 1994

[54] METHODS AND APPARATUS FOR USE IN ALPHA TRAINING, EMG TRAINING AND DICHOTIC LEARNING

[76] Inventor: Joseph N. Trachtman, 26 Schermerhorn St., Brooklyn, N.Y. 11201

[21] Appl. No.: 526,167

[22] Filed: May 21, 1990

Related U.S. Application Data

[63] Continuation-in-part of Ser. No. 1,337, Jul. 7, 1987, Pat. No. 5,002,384, which is a continuation-in-part of Ser. No. 829,555, Feb. 13, 1986, Pat. No. 4,660,945, which is a continuation of Ser. No. 716,025, Mar. 25, 1985, abandoned, which is a continuation of Ser. No. 460,850, Jan. 25, 1983, Pat. No. 4,533,221.

[51] Int. Cl.⁵ ............................................. G09B 19/00
[52] U.S. Cl. .................... 434/258; 434/238; 351/210; 351/203; 128/731; 128/732; 364/413.02
[58] Field of Search ............. 128/630, 732, 731, 765; 351/203, 210, 208, 211, 213, 214, 246; 434/258, 236, 238, 43, 44, 262; 273/440, 454; 364/413.01, 413.02, 413.06, 413.27; 340/573; 358/93; 73/379

[56] References Cited

U.S. PATENT DOCUMENTS

| | | | |
|---|---|---|---|
| 3,942,516 | 3/1976 | Glynn et al. | 128/732 |
| 4,105,302 | 8/1978 | Tate, Jr. | 351/210 |
| 4,228,807 | 10/1980 | Yagi et al. | 128/732 |
| 4,319,239 | 3/1982 | Stephens | 350/334 |
| 4,533,221 | 8/1985 | Tractman | 351/203 |
| 4,660,945 | 4/1987 | Tractman | 351/203 |
| 4,720,189 | 1/1988 | Heynen et al. | 351/210 |
| 4,736,751 | 4/1988 | Gevins et al. | 128/732 |
| 4,755,045 | 7/1988 | Borah et al. | 351/210 |
| 4,852,988 | 8/1989 | Velez et al. | 351/210 |
| 4,928,696 | 5/1990 | Henderson et al. | 128/791 |
| 4,955,388 | 9/1990 | Silberstein | 128/731 |
| 5,036,858 | 8/1991 | Carter et al. | 128/732 |

FOREIGN PATENT DOCUMENTS

| | | |
|---|---|---|
| 0199218 | 10/1986 | European Pat. Off. |
| 8000405 | 3/1980 | U.S.S.R. ............... 351/203 |

OTHER PUBLICATIONS

"VEP Measurement of the Amplitude of Accommodation" by Willodot et al, British, Journal of Ophthalmology, 1981, 65, pp. 294–298.

"Coincidence Eye Position Device With Applications in Clinical Psychophysics, Eye-position Traning and Visual Evoked Response Recording" by Genter II et al, Medical & Biological Engineering & Computing, Jul. 1981, 19, pp. 509–513.

*Primary Examiner*—Richard J. Apley
*Assistant Examiner*—Joe H. Cheng

[57] ABSTRACT

Accommodation training apparatus is modified to include electroencephalography apparatus for monitoring the patient's brainwaves. This permits a patient to be trained to enter, and to remain in, the alpha state, even with the eyes open and with something to look at.

A two-dimensional CCD matrix is used to receive reflected-back radiation from the eye. A computer is connected to the matrix and permits the patient to be trained for correction of conditions such as strabismus, nystagmus and eccentric fixation by identifying whether the patient's eye is moving or whether the patient's state of accommodation is changing.

An LCD matrix is used to present variable visual information to the patient's eye. This facilitates training the patient for dichotic learning.

Advantageously, electromyography apparatus is used to monitor the tension of one of the patient's muscles, advantageously the frontalis muscle.

25 Claims, 8 Drawing Sheets

METHODS AND APPARATUS FOR USE IN ALPHA TRAINING, EMG TRAINING AND DICHOTIC LEARNING

CROSS-REFERENCE TO RELATED APPLICATIONS

This application is a continuation-in-part application of my application Ser. No. 1,337 filed Jan. 7, 1987 and now U.S. Pat. No. 5,002,384, which is a continuation-in-part application of my application Ser. No. 829,555 filed Feb. 13, 1986 and now U.S. Pat. No. 4,660,945, which is a continuation of my application Ser. No. 716,025 filed Mar. 25, 1985 and now abandoned, which is a continuation of my application Ser. No. 460,850 filed Jan. 25, 1983 and now U.S. Pat. No. 4,533,221.

BACKGROUND OF THE INVENTION

The invention relates to brainwave training, electromyography training, dichotic learning and accommodation training.

It is known that then a subject is in the alpha state (i.e. is in the state in which the brain emits alpha waves), the subject's performance improves; nervous tension is reduced, reaction times decrease, attention becomes heightened, etc. Alpha training has consequent been investigated as a technique by which, e.g., athletic performance can be improved.

However, alpha training has heretofore been carried out with the subject's eyes closed. This is because it has generally been believed that a subject cannot enter the alpha state then the subject has open eyes and something to look at. As a result, persons those performance depends upon vision (e.g. fighter pilots, target shooters etc.) have heretofore been unable to benefit from open-eye alpha training.

The present invention proceeds from the discovery that existing beliefs regarding the alpha state are erroneous. In particular, the present invention proceeds from the discovery that a subject can be trained to enter the alpha state not only with eyes open, but with the eyes detected upon a visual image. Furthermore, the present invention proceeds from the discovery that accommodation training is—contrary to conventional wisdom in the art—a most efficient way in which to accomplish alpha training.

Brainwave training is also considered useful for children with learning disabilities. Such children tend to be in the theta state (i.e. in the state in which their brains emit theta waves) and also tend to be hyperopic. It has now been discovered that such children may be treated by alpha training, implemented by accommodation training.

As previously practiced, accommodation training has been directed to improving the subjects vision. U.S. Pat. No. 4,162,828 discloses apparatus which directly measures, in real time, the refraction of the eye. U.S. Pat. Nos. 4,533,221 and 4,660,945 disclose that apparatuses of this type can, with appropriate use of biofeedback techniques, be used to train a patient to improve his or her visual focusing ability even in the absence of corrective lenses. In these devices, the refraction of the eye is measured and used to produce a tone to which the patient may listen. The patient may then be trained to be able to control his eye focusing by, e.g., learning how to drive up the pitch of the tone. Training programs of this sort are known by the general term "accommodation training".

It has now been discovered that accommodation training can be used for alpha training, and not merely for vision improvement. It can now be shown that most if not all subjects have an accommodation window. When the subject focuses to an accommodation level which is within this window, the subject's muscle tension diminishes and the subject enters the alpha state. The accommodation training is so programmed that the subject is taught how to enter the alpha state so as to facilitate entry into the alpha state when this is required by the performance demands of, e.g., athletic competition, air combat, etc.

Individuals such as fighter pilots, etc. are required to process many channels of information simultaneously. For example, if a pilot spots a potential threat, he must determine from the threat's behavior whether the threat is hostile or not. Additionally, the pilot must be aware of the condition of his aircraft and must be prepared, as required, to respond to commands from his superiors, to take evasive action or to attack the threat. To accomplish all these objectives simultaneously, the pilot must be able to, e.g., interpret the outputs from his instrument panel, to hear and respond to commands from his communications equipment, to steer and control his aircraft and to monitor the behavior of the threat, all at the same time.

This cognitive process, by which a subject learns to deal with different channels of information simultaneously, is known as dichotic learning. It has now been discovered that by modifying apparatus which was previously used for accommodation training alone, a subject can be trained in dichotic learning.

One object of the invention is to improve existing apparatus for accommodation training so as to make it useful for open-eye alpha training of patients (like Olympic athletes and fighter pilots) who entirely lack common vision disorders. Another object is to improve existing apparatus for accommodation training so as to make it useful for training patients in dichotic learning.

Still another object is to generally improve on known equipment of this general type.

In accordance with one aspect of the invention, conventional accommodation training equipment is modified by providing electroencephalography (EEG) apparatus for monitoring of a patient's brainwaves. By teaching the patient to remain in the alpha state while performing vision and/or hearing related exercises, the patient may be trained to enter and remain in the alpha state where circumstances require this or make it advantageous. In preferred embodiments, electromyography (EMG) apparatus is also provided for monitoring muscle tension; such apparatus advantageously monitors the tension of the frontalis muscle and may also be used to monitor the tension of other muscles as well.

In accordance with another aspect of the invention, EMG training can be carried out using the electromyography apparatus referenced above. This is useful when the patient reaches a plateau where progress in alpha training is temporarily blocked.

In accordance with still another aspect of the invention, conventional accommodation training equipment is modified by providing apparatus to project images onto the patient's eyes in response to video signals. This permits the patient to be trained in dichotic learning.

In accordance with a further aspect of the invention, a two-dimensional photosensitive matrix, such as a two-dimensional CCD matrix, is used instead of the linear CCD array which has been used before. This has the unexpected advantage that, by using a computer, it becomes possible to distinguish between changes in accommodation and changes in eye position. As a result, it is possible to train individuals who suffer from multiple vision disorders. Additionally, it is much easier to use the apparatus because the computer can be programmed to register baseline information about the patient and to monitor, on a real time basis, deviations from such baseline information. This avoids the need for repeated manual readjustments of the apparatus, which would otherwise be necessary.

BRIEF DESCRIPTION OF THE DRAWINGS

The invention will be better understood with reference to the following illustrative and non-limiting drawings, in which.

DETAILED DESCRIPTION OF A PREFERRED EMBODIMENT

Known accommodation training apparatus, such as that disclosed in U.S. Pat. Nos. 4,533,221 and 4,660,945 will initially be described in connection with FIG. 1.

Figure 1:
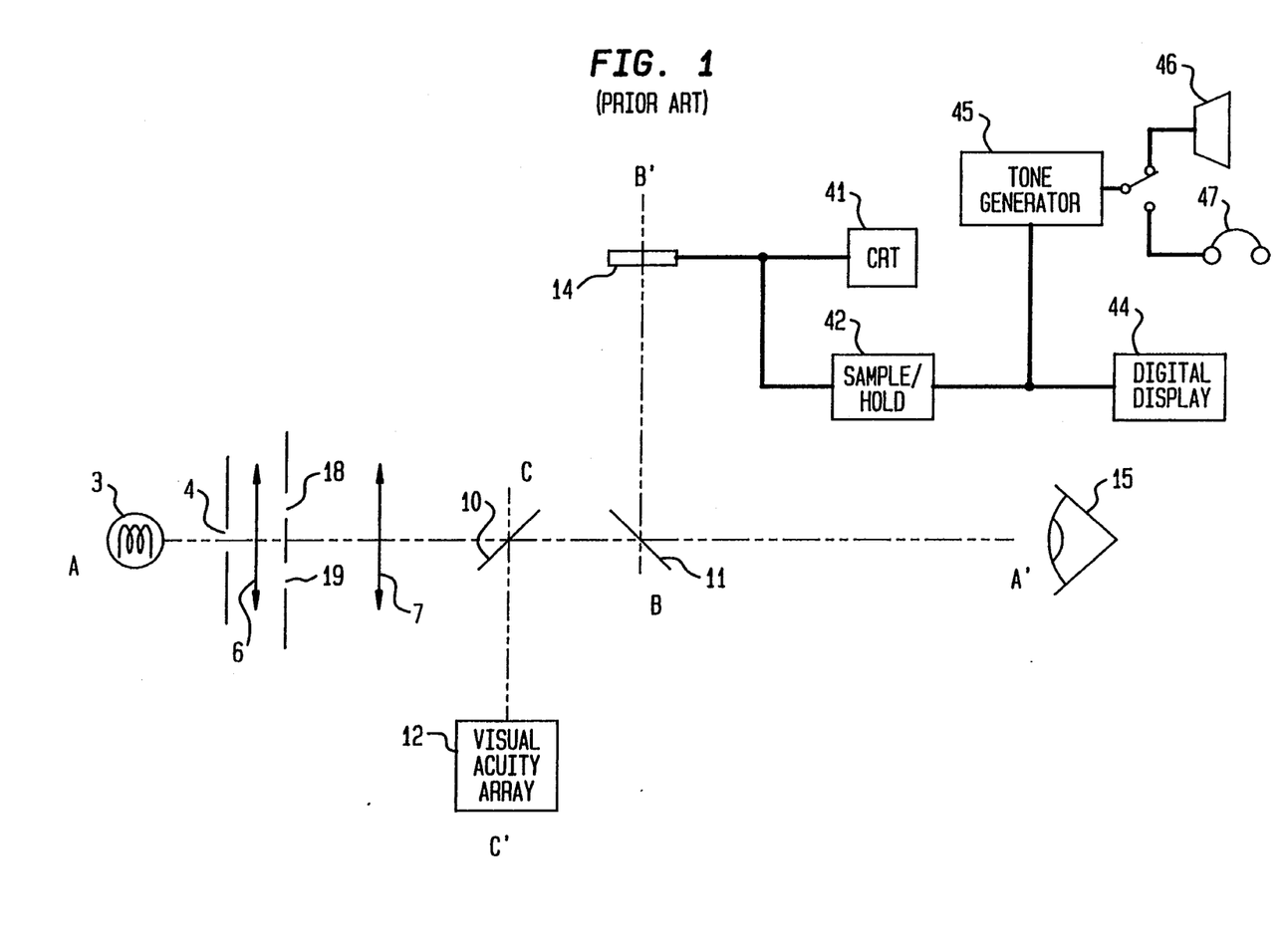
FIG. 1 is a schematic illustration of known apparatus used in accommodation training.

In known apparatus, light is projected along axis A—A' and through beam splitters 10 and 11 to become incident upon an eye 15. The light is then reflected back by the cornea and retina (not shown) of the eye 15, and the reflected-back light is directed along axis B'–B by the beam splitter 11 to become incident upon a CCD sensor array 14. (For the purposes of accommodation training, only retinal reflection is important, and as a result of the optics hereinafter disclosed, the results produced by the preferred embodiment are dominated by retinal, rather than corneal, reflection.)

During accommodation training, infra-red light from an IR source 3 is passed through, inter alia, a first slit 4 and then two closely-spaced slits 18 and 19. Lenses 6 and 7 make the IR light parallel after lens 7 so that the light is parallel when it is incident on the eye 15. Lens 7 images the slits 18 and 19 onto the plane of the pupil of the eye 15. (Such focusing onto the plane of the pupil is known as Maxwellian View.)

In accordance with Scheiner's principle, the characteristics of the eye 15 determine how the images of the slits 18 and 19 will be focused on the retina of the eye 15. If the eye is emmetropic (i.e. neither nearsighted nor farsighted), an image of the slit 4 will be formed on the retina of the eye 15. If the eye 15 is myopic (nearsighted), the image of the slit 4 will be focused in front of the retina of the eye 15. The image of the slit 4 will appear double on the retina of the eye 15 and the separation between them on the retina of the eye 15 will be directly proportional to the degree of myopia. If the eye 15 is hyperopic (farsighted), the image of the slit 4 will be focused behind the retina of the eye 15. The image of the slit 4 will appear double on the retina of the eye 15 and the separation between them on the retina of the eye 15 will be directly proportional to the degree of hyperopia. In the case of a farsighted eye, the images of the slit 4 will be displayed on the array 14 closer together than in the case of a nearsighted eye.

Figure 2:
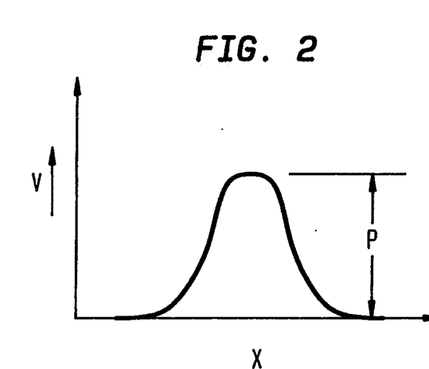
FIG. 2 illustrates the waveform which is output from the linear CCD array when the accommodation of an emmetropic eye is being monitored.
Figure 3:
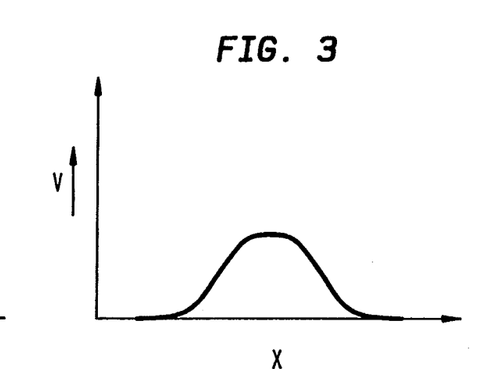
FIG. 3 illustrates the waveform which is output from the linear CCD array when the accommodation of a myopic eye is being monitored.
Figure 4:
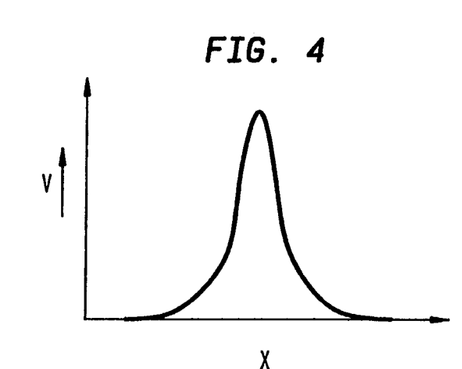
FIG. 4 illustrates the waveform which is output from the linear CCD array when the accommodation of a hyperopic eye is being monitored.

Consequently, as is shown in FIGS. 2, 3 and 4, the output of the array 14 indicates the existence of any ametropia (refractive anomaly) of the eye 15 and indicates the severity of such ametropia if it exists. It will be understood that the sharpness of the images of the slit 4 is not reproduced at the array 14. This is because there are light reflections inside the eye 15 and diffusion of the images consequently takes place.

Research has shown that for purposes of accommodation training, the most significant component of the output of the array 14 is the peak voltage P. For each readout of the array 14, this peak voltage P is held and used to establish the frequency (pitch) and/or rate (variation of volume as a function of time) of an audio tone which is presented to the patient by way of a speaker 46 or earphones 47. The readouts occur sufficiently frequently (advantageously 40 times per second) that the pitch of the tone changes in a continuous, rather than a discrete, fashion. In one aspect of accommodation training, the patient is instructed to drive the tone up or to keep the tone at a particular rate. When the patient does this, he or she learns to exercise control over the accommodation of the eye 15. For those patients who desire to drive the tone down instead of up, the control panel 154 described below makes it possible to reverse the direction in which the tone changes.

In this known apparatus, the beam splitter 10 is part of a Badal optometer. Individual elements of an array 12 of, e.g., Snellen characters can be selectively illuminated; the resulting images are projected along axis C'—C and directed onto the eye 15.

Although the above-described apparatus (presently sold under the registered ACCOMMOTRAC trademark by Biofeedtrac Inc., 26 Schermerhorn Street, Brooklyn N.Y. 11201) has achieved substantial commercial success, it has certain drawbacks. One drawback is that the optical system must be repeatedly repositioned to maintain alignment with the patient's eye. Another drawback is that the biofeedback tone itself is not unambiguously reflective of but a single variable, since the tone can change not only as a result of a change in accommodation but also of eye position.

Additionally, the above apparatus was originally intended for use in training persons with vision disorders. It would be advantageous to be able to use it to improve the performance of athletes and others who lack such disorders.

The preferred embodiment of the invention will be discussed next. In view of the complexity of the subject matter, the optical elements of the preferred embodiment will be discussed first. This discussion will be followed by an explanation of the workings of the output side of the preferred embodiment. Thereafter, the input side of the preferred embodiment will be explained. After this explanation has been accomplished, the brainwave/muscle tension monitoring apparatus will be described. This description will then be followed by a short illustration of learning methods which are designed to subject a patient to alpha training and training for dichotic learning.

Figure 5:
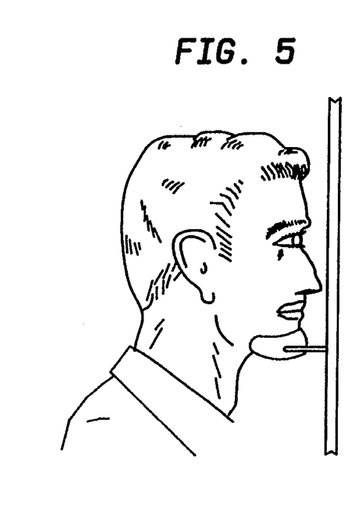
FIG. 5 is a schematic sketch of a head and chin rester.
Figure 6:
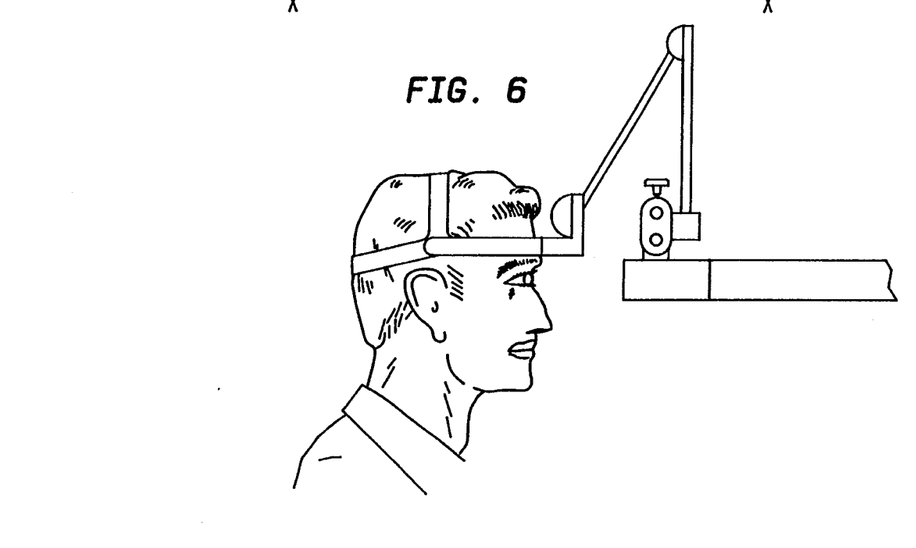
FIG. 6 is a schematic sketch of an ophthalmic headband and an articulated arm.
Figure 7:
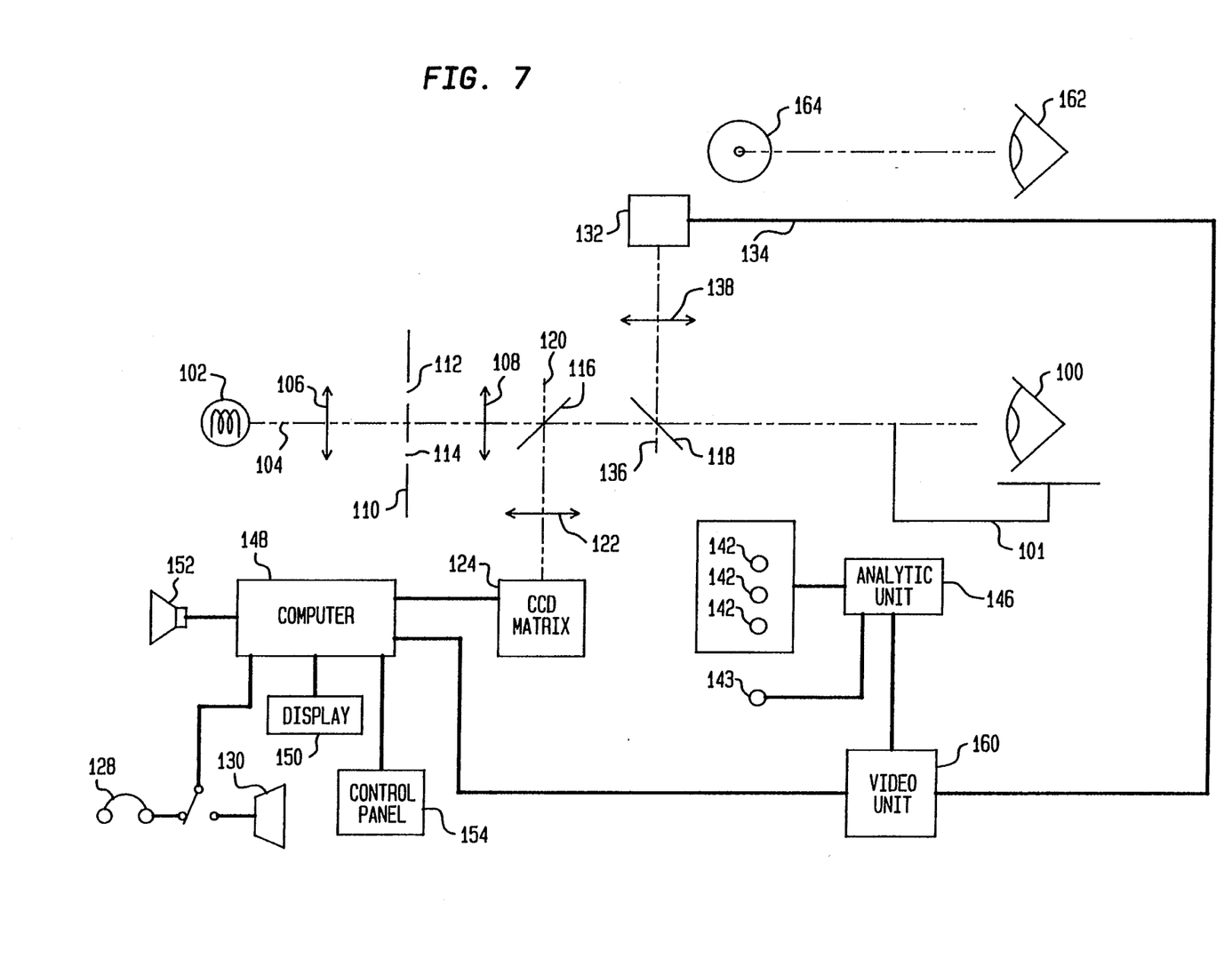
FIG. 7 is a block diagram of a preferred embodiment in accordance with the invention.

In the preferred embodiment shown in FIG. 7, it will be understood that the head (not shown) of the patient is linked with the optical system so as to maintain alignment between the optical system and the eye 100. Where the optical system is fixed and rests for example upon a table or stand, this may be accomplished by using a head and chin rester (FIG. 5). Alternatively, if the optical system is made lightweight, this may be accomplished by an ophthalmic headband and articulated arm (FIG. 6). Whichever linkage mechanism is used, the mechanism is schematically indicated by a connection (reference numeral 101) between the eye 100 and optical axis 104.

An infrared light-emitting diode 102 serves as a source of light. The light is directed along optical axis 104 through a pair of lenses 106 and 108. Each lens 106 and 108 is a condensing lens with a focal length of 50 mm; the lenses are achromatic doublets. The lens 106 is 100 mm forward of the LED 102 and the lens 108 is 150 mm forward of the lens 106. The lenses 106 and 108 make the light from the LED 102 parallel and the image of the LED 102 is focused 50 mm forward of the lens 108.

A slotted plate 110 is located between the lenses 106 and 108; the plate 110 is 50 mm forward of the lens 106 and consequently is 100 mm rearward of the lens 108. The plate 110 has two slits 112 and 114; the slits 112 and 114 are each 1.5 mm wide and are separated by 1 mm so that each of the slits 112 and 114 is displaced by 0.5 mm from the axis 104. This arrangement causes the slits 112 and 114 to be imaged onto the pupil of the eye 100 in Maxwellian View, after the light passes through beam splitters 116 and 118.

Reflected-back light from the eye 100 (most of the reflection is from the retina of the eye 100) passes rearwardly along the axis 104 through the beam splitter 118 and is reflected by the beam splitter 116 along axis 120, which is normal to the axis 104. The reflected-back light then passes through a lens 122, which in this example is an achromatic doublet or triplet with a focal length of 43 mm. The lens 122 is spaced 50 mm distant from the beam splitter 116.

The lens 122 focuses the light and projects it onto a two-dimensional charge-coupled device matrix 124. In this example, the CCD matrix is advantageously 512×486 and is 70 mm distant from the lens 122, but these dimensions are not part of the invention.

Figure 9:
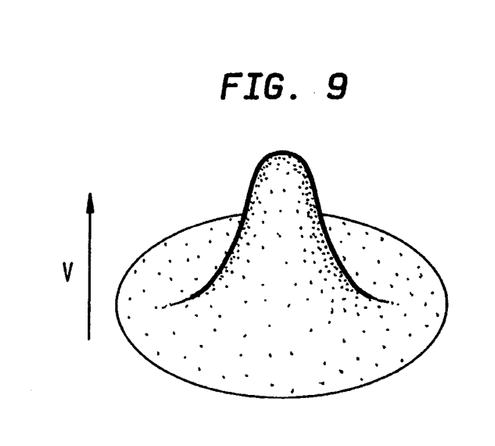
FIG. 9 illustrates the output of the CCD array of the preferred embodiment in the case of an emmetropic eye.
Figure 10:
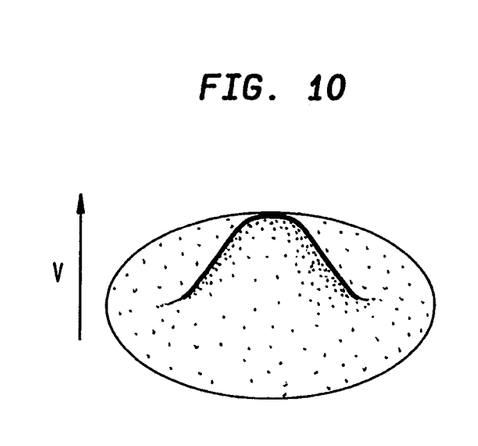
FIG. 10 illustrates the output of the CCD array of the preferred embodiment in the case of an myopic eye.
Figure 11:
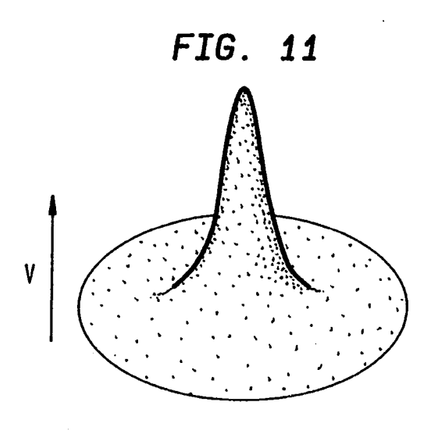
FIG. 11 illustrates the output of the CCD array of the preferred embodiment in the case of a hyperopic eye.

When the preferred embodiment of the invention is used to monitor accommodation of the eye 100, the image appearing on the CCD matrix 124 will identify whether the eye 100 is emmetropic, myopic or hyperopic. An emmetropic eye 100 will cause the image of the LED 102 to be imaged on the CCD matrix 124 as is shown in FIG. 9. A myopic eye 100 will cause the image of the LED 102 to be imaged on the CCD matrix 124 as is shown in FIG. 10, while a hyperopic eye 100 will cause the image of the LED 102 to be imaged on the CCD matrix 124 as is shown in FIG. 11.

For an eye in which no astigmatism is present, the reflections from the retina are radially symmetrical with respect to the pupil. Consequently, FIG. 9 is the result of rotating FIG. 2 about its center and FIGS. 10 and 11 are, respectively, rotated versions of FIGS. 3 and 4.

To coarsely align the eye 100 with the axis 104, an alignment pattern is projected onto the iris of the eye 100. Then, the head and chin rester or ophthalmic headband 101 is adjusted so as to center the alignment pattern around the pupil of the eye 100.

The pattern is created by an array of light sources which is radially symmetrical about the axis 104 and which surrounds the plate 110. Advantageously, these light sources are LED's (not shown), and there may be as few as three (to form a triangular alignment pattern) or many more (to form, e.g., a ring).

Figure 12:
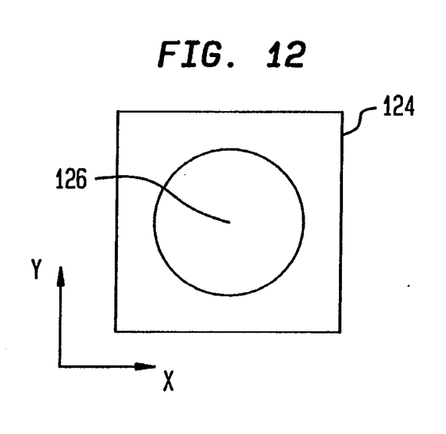
FIG. 12 illustrates the pattern projected onto the CCD array of the preferred embodiment in the case of a non-astigmatic eye.
Figure 13:
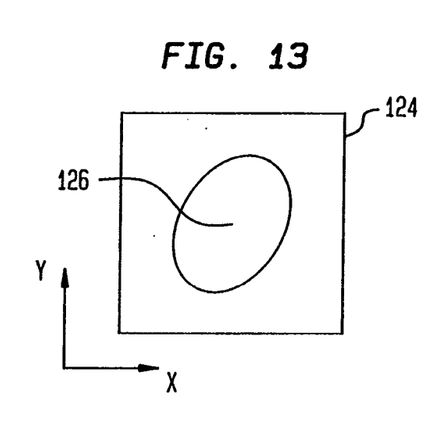
FIG. 13 illustrates the pattern projected onto the CCD array of the preferred embodiment in the case of an astigmatic eye.

After coarse alignment of the eye 100 has been carried out it is optionally possible to perform a fine alignment of the eye 100. This is done by centering the image which is displayed on the display 150 described below. An image such as that shown in FIGS. 9, 10 or 11 will be formed on the CCD matrix 124, but will likely be offset with respect to the center 126 of the CCD matrix 124 (see FIGS. 12 and 13). By appropriate adjustment of the head and chin rester or ophthalmic headband 101 the image can be centered on the center 126 of the CCD matrix 124 and thereby on the display 150.

The above descriptions have proceeded on the assumption that the eye 100 undergoing examination/training is devoid of astigmatism. Astigmatism is manifested by an asymmetry of the cornea or other optical elements of the eye. Thus, when a nonastigmatic eye 100 is undergoing examination/training and the above-referenced alignment ring is properly centered on the eye 100, the image of the circular IR LED 102 will be projected into the eye 100, refracted by the eye 100, reflected by beam splitter 116, and finally focused by the lens 122 onto the CCD matrix 124 as a circular pattern (see FIG. 12). Where the eye 100 is astigmatic, the pattern on the CCD matrix 124 will be elliptical (FIG. 13), the direction and eccentricity of the ellipse indicating the nature and severity of the astigmatism.

Figure 14:
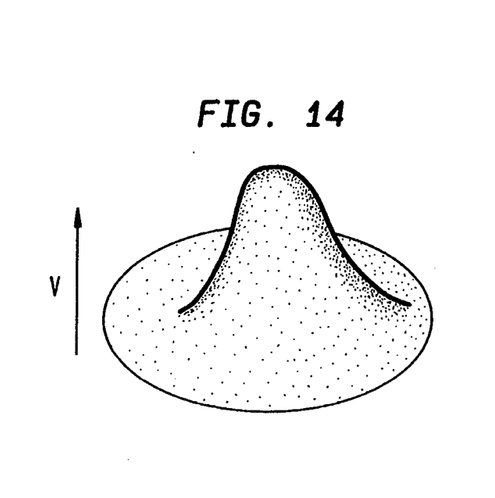
FIG. 14 shows the output of the CCD matrix for an emmetropic eye which is nonaligned with respect to the axis.
Figure 15:
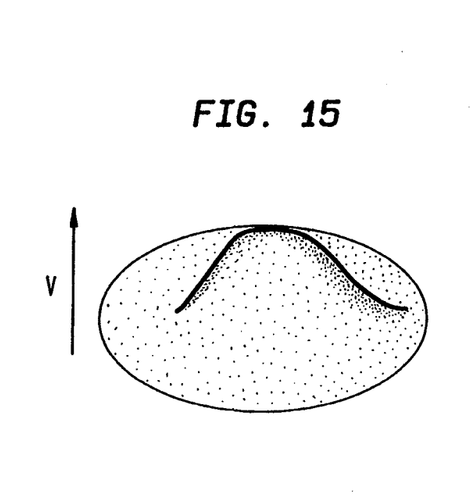
FIG. 15 shows the output of the CCD matrix for a myopic eye which is nonaligned with respect to the axis.
Figure 16:
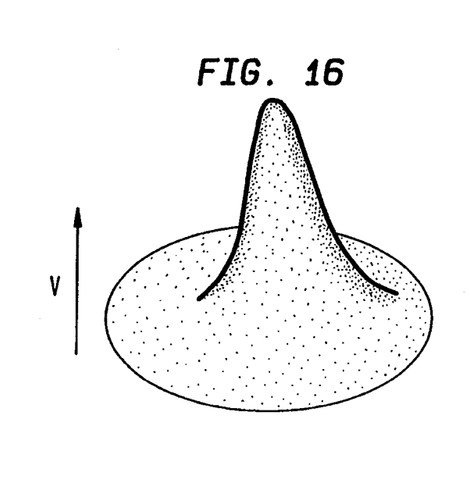
FIG. 16 shows the output of the CCD matrix for a hyperopic eye which is nonaligned with respect to the axis.

The orientation of the eye 100 with respect to the axis 104 will affect the image which is projected onto the CCD matrix 124. Where the eye 100 is aligned with respect to the axis 104, the output of the CCD matrix is as shown above in FIGS. 9, 10 and 11. Where the eye 100 is nonaligned with respect to the axis 104, the output of the CCD matrix 124 is as shown in FIGS. 14 (emmetropic case), 15 (myopic case) and 16 (hyperopic case). In the nonaligned cases, the output of the CCD matrix is not symmetric as in the instances of FIGS. 9, 10 and 11; it is rather skewed. The degree of skew is related to the degree of nonalignment.

It will become apparent that the information at the output of the CCD array 124 represents the condition of the patient's eye 100 in respect of accommodation, eye rotation with respect to the head, position of the head with respect to the optical system, etc. Exemplary uses which may be made of this information will now be described.

Figure 17:
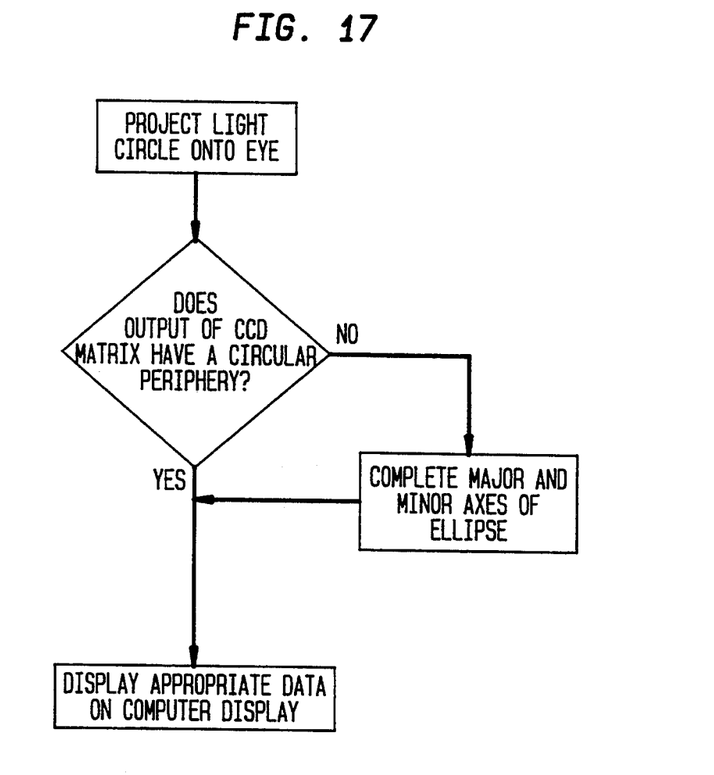
FIG. 17 shows one program which may advantageously be executed by the computer.

A computer 148 is connected to the CCD matrix 124. The computer 148 is programmed to register the output of the CCD matrix 124 and to register differences between the outputs of the CCD matrix 124 as needed by the trainer and the patient. In one exemplary program which is schematically shown in FIG. 17, a circle of light is projected onto the eye 100 (whether by use of the coarse alignment procedure described above or by one of the LCD matrices 140). The output of the CCD matrix 124 (which will be a circle or an elliptical pattern) is then registered by the computer 148. If the output is such as to qualify for treatment as a circle, this is displayed on the computer display 150. If the output is such as to be treated as elliptical, the computer determines the major and minor axes of the ellipse and displays the appropriate information on the display 150.

Figure 18:
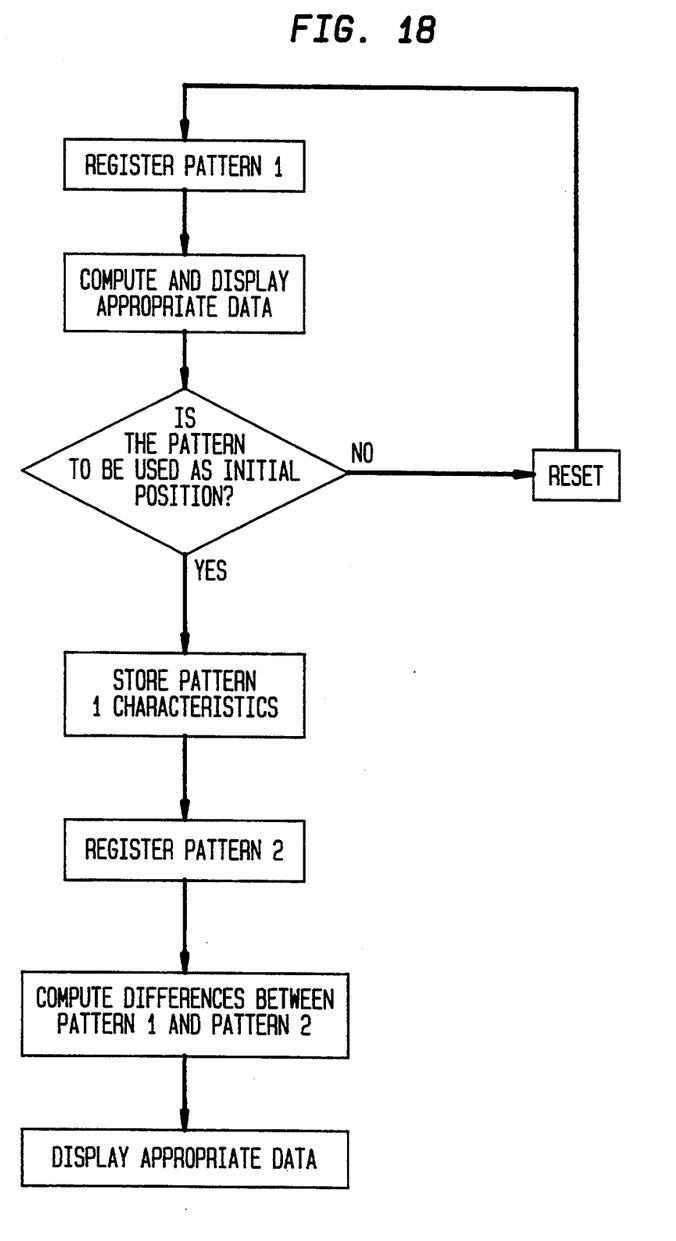
FIG. 18 shows another program which may advantageously be executed by the computer.

As training (described below) progresses, the trainer and patient need to know whether, and how, the patient's accommodation and eye position are changing. One exemplary manner in which the computer 148 may be programmed to accomplish this is schematically illustrated in FIG. 18. As is shown there, the trainer registers an initial pattern by operating the control panel 154. This causes the necessary information about the pattern (e.g. symmetry, kurtosis, peak voltage, volume, coordinates of center) to be either registered or computed and displayed on the display 150. (The invention does not reside in the type of information, such as symmetry, kurtosis, peak voltage, volume, coordinates of center, which is registered or computed.) Additionally, and as is described below, this information can be used for biofeedback; where peak voltage is sampled and held as representative of a patient's accommodation, this voltage may be used to, e.g., determine the frequency of a tone and/or the rate of a sound which is presented to the patient.

During examination/training, the initial pattern is reset as desired. Then, when the trainer decides to select a subsequent pattern by operating the control panel 154, the differences between the initial and subsequent patterns are computed and read out on the display 150. Thus, if for example the symmetry of the pattern and the coordinates of the center of the pattern change in a related way, the computer may output an indication that the patient's eye has rotated from axial alignment to a specified direction of nonalignment. Alternatively, if the symmetry of the pattern does not change but the coordinates of the center do change, the computer may output an indication that the patient's head has moved while the patient's eye has remained fixed with respect to the head.

In a manner similar to that employed in the referenced U.S. Pat. Nos. 4,533,221 and 4,660,945, the peak voltage produced by one of the photodiodes in the matrix 124 during a single readout cycle may be held until completion of the next cycle and used to determine the pitch of an audio tone which can be presented to the patient via headphones 128 or speakers 130. This may be implemented by software in the computer 148 or may alternatively be implemented by use of a separate voltage-controlled oscillator (not shown). Alternatively, if the patient is being trained for such conditions as strabismus, nystagmus or eccentric fixation, the distance of the center of the pattern on the CCD matrix 124 and the center 126 of the CCD matrix may for example be used to control the referenced tone.

The above description has concentrated on the output side of the preferred embodiment, i.e. on what happens to light which is reflected from the eye 100 of the patient. The input side of the preferred embodiment will be described next.

A Badal optometer channel includes a display unit 132, which forms an image from a video signal fed along line 134 and projects that image along axis 136 through a lens 138 onto the beam splitter 118. The beam splitter 118 reflects the image along the axis 104 to the eye 100. The display unit 132 (see FIG. 8) contains a plurality, advantageously 5, liquid crystal display matrices 140, all of which are differently spaced with respect to the lens 138 so as to present images of varying dioptric stimuli (blur cue information) to the eye 100 when the lamp 139 is energized. The use of LCD matrices 140 permits great flexibility in the blur cue information presented to the patient; in the ACCOMMOTRAC® Vision Trainer, LCD plates are used instead, limiting the blur cue information to the predetermined images which are displayed when the plates are activated. An LCD matrix such as that used for matrices 140 can display anything which can be displayed on a computer screen.

Figure 8:
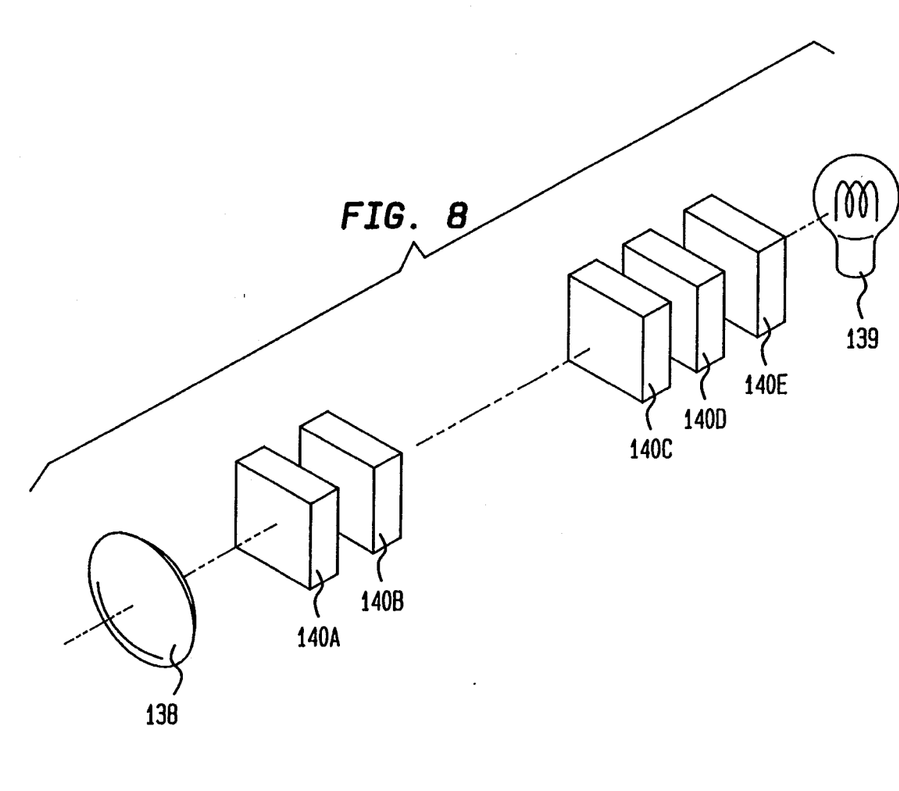
FIG. 8 is a detail view of the display unit in the preferred embodiment.

The video signals provided to the display unit 132 are generated by a video unit 160. This unit 160 may be implemented as a board in the computer 148 or as a separate component; it is shown as an independent block only for the sake of clarity. Furthermore, while line 134 is shown as a single line, it will be understood that this is actually a data bus because video information will normally be displayed on only one of the LCD matrices 140 at a time (although in situations—accommodative rocking—where the patient is instructed to change accommodation between two different states, two or more of the LCD matrices 140 may be energized simultaneously). Thus, if the trainer wishes to cause a Snellen "E" character to be displayed at a 3.00 Diopter stimulus, LCD matrix 140A might be energized with a Snellen "E". Should the trainer wish to cause the same character to be displayed at a 0.00 Diopter stimulus, the same video information would be generated by the video unit 160 but routed to LCD matrix 140D instead. Alternatively, if the trainer wished to cause the same character to be displayed at a −0.75 Diopter stimulus, LCD matrix 140E might be energized. In such cases, the trainer inputs appropriate information on the control panel 154 and the computer 148 and video unit 160 cooperate in such a manner as to appropriately energize the appropriate one of the LCD matrices 140. Further alternatively, the pattern displayed on the LCD matrices 140 may be kaleidoscopic or may vary in rate or shape in accordance with the state of accommodation of the patient's eye or other factor.

In addition to the optical input and output sides of the preferred embodiment, there is also provided apparatus which monitors the patient's brainwaves and the muscle tension in one or more of the patient's muscles. This apparatus will be described next.

In the preferred embodiment, the head and chin rester or ophthalmic headband 101 contains three electrodes 142 and a reference ground 143 to clip on the ear of the patient. Electrodes 142 touch the patient's forehead when the patient is properly positioned and picks up the EEG information from the patient's brain and EMG information from the patient's frontalis muscle. (It is preferred if the electrodes 142 touch the forehead, but this is not necessary. It is preferred because such placement permits EEG and EMG information to be derived from the same electrodes.) The output from the electrodes 142 is used to classify the brainwaves between alpha (8–13 Hz, a measure of alertness) beta (>14 Hz, the normal waking state) delta (0.5–3 Hz, the sleep state) and theta (4–7 Hz, the creative state). In the preferred embodiment, this is carried out by an analysis unit 146 which is known to persons skilled in the art, but this is not necessary and the classification scheme may alternatively be implemented in software in the computer 148.

The electrodes 142 also act as an electromyogram sensor for the frontalis muscle. Appropriate circuitry is advantageously contained in the analysis unit 146 since EMG signals have frequencies on the order of 200 Hz and are consequently distinguishable from brainwaves. The tension in the frontalis muscle is a measure of the tenseness or relaxation of the patient. When a patient's head is not properly positioned in the head and chin rester or ophthalmic headband, the absence of corresponding signals at any of the electrodes 142 causes an alarm 152 to indicate the improper positioning.

When the preferred embodiment is used for alpha training, the patient is instructed to relax and to enter the alpha state. Once the patient has done so, the patient is given various tasks to perform without leaving the alpha state. For example, the patient may be requested to drive the tone or rate up or down or to maintain it at an existing level without leaving the alpha state. If the tone is responsive to accommodation of the eye 100, the training will relate accommodation to the alpha state. If the tone is responsive to position of the eye 100, the training will relate eye position to the alpha state. If desired, the existence or lack of an alpha state and/or muscle tension in the frontalis and/or other muscle may be visually indicated to the patient by causing appropriate visual indications to appear or be absent from the visual stimulus displayed to the patient's eye 100 on the LCD matrices 140. This is done by appropriate connections between the analysis unit 146, video unit 160 and computer 148.

When the preferred embodiment is used to improve dichotic learning, a reference stimulus is provided to the untrained eye or ear associated therewith and a variable stimulus (an audible tone from the earphones 128 or speaker 130 or a visual display on an LCD matrix 140) is provided to the eye which is to be trained. The variable stimulus is varied in accordance with the state (accommodation, position) of the eye being trained, and the patient is instructed to make the stimuli match. For example, the left (untrained) ear may be provided with a constant auditory signal and the patient may be instructed to make a variable auditory signal (which varies in pitch depending upon the accommodation of the right eye) match the constant auditory signal.

To facilitate training, it is advantageous to provide some means to anchor the position of the eye 162 (FIG. 7) which is not being trained. This may be done by providing a target 164 for the eye 162 and instructing the patient to look at it. The target 164 may itself be an LCD matrix, but this is not required.

Persons skilled in the art will be able to adapt the above training principles to formulate suitable programs for individual patients.

Although a preferred embodiment has been described above, the scope of the invention is limited only by the following claims:

I claim:

1. A biofeedback device for use in accommodation training of a patient's eyes, comprising:
means for detecting, in real time and for one of the patient's eyes, at least one parameter of interest;
means for detecting the patient's brainwaves;
means for evaluating said at least one parameter in accordance with pre-established criteria, said evaluating means being operatively connected to said means for detecting for one of the patient's eyes at least one parameter of interest and operating to evaluate said at least one parameter in real time; and
means for producing an audio output, said audio output means being operatively connected to said evaluating means and operating in real time as a part of a biofeedback system.

2. A biofeedback device for use in accommodation training of a patient's eyes, comprising:
means for detecting, in real time and for one of the patient's eyes, at least one parameter of interest;
means for detecting the patient's brainwaves;
means for evaluating said at least one parameter in accordance with pre-established criteria, said evaluating means being operatively connected to said means for detecting for one of the patient's eyes at least one parameter of interest and operating to evaluate said at least one parameter in real time; and
means for producing a visual output, said visual output means being operatively connected to said evaluating means and real time as a part of a biofeedback system.

3. The device of claim 1 or claim 2, further comprising means for monitoring an electromyogram of one of the patient's muscles.

4. The device of claim 3, wherein said monitoring means comprises means for monitoring the patient's frontalis muscle.

5. The device of claim 3, further comprising means for mechanically linking, with the patient's head, said means for detecting for one of the patient's eyes at least one parameter of interest, and wherein electrodes for said brainwave detecting means and said monitoring means are mounted to said mechanical linking means in such a position as to make operative electrical contract with the patient when the patient's head is properly positioned on said mechanical linking means.

6. The device of claim 5, wherein said mechanical linking means is a head and chin rester.

7. The device of claim 5, wherein said mechanical linking means is an ophthalmic headband with an articulated arm.

8. The device of claim 5, further comprising means for indicating when the patient's head fails to make operative contact with said electrodes.

9. The device of claim 1, wherein said parameter detecting means comprises:

means for projecting light onto the eye; and means for detecting light which is reflected back from the eye.

10. The device of claim 9, wherein said light detecting means includes a two-dimensional CCD matrix.

11. The device of claim 9, wherein said projecting means comprises means for projecting a parallel beam of light onto the eye in Maxwellian View.

12. The device of claim 9, wherein said projecting means comprises means for producing a video image and means for projecting said image onto the eye.

13. The device of claim 12, wherein said video image producing means comprises a two-dimensional LCD matrix.

14. The device of claim 12, wherein said evaluating means comprises a computer and wherein said video image producing means is operatively connected to the computer in such a manner as to produce a video image in response to electrical signals outputted by the computer.

15. The device of claim 9, further comprising means for projecting an alignment pattern upon the iris of the eye.

16. A device for use in accommodation training of a patient's eye, comprising:

an adjustable frame for aligning the device with the patient's eye;

means for projecting an alignment image onto the iris of the eye, whereby adjustment of said frame is facilitated;

means for projecting a blur cue image one the eye, said blur cue projecting means including video image producing means for producing an image from a video signal;

optical focusing means, said optical focusing means being in operative optical relationship with the eye and focusing, to a predetermined plane, light reflected from the eye;

a two-dimensional photosensitive array located in said predetermined plane;

a computer operatively connected to the photosensitive array; and means for detecting the patient's brainwaves, said brainwave detecting means being connected to the computer and having electrodes which are mounted to said frame so as to make operative electrical contact with the patient when the patient's head is properly positioned on the frame.

17. The device of claim 16, further comprising means for monitoring an electromyogram of the patient's frontalis muscle, said monitoring means having electrodes which are mounted to said frame so as to make operative electrical contact with the patient when the patient's head is properly positioned on the frame.

18. The device of claim 16, further comprising video display means which displays a representation of light focused upon the photosensitive array.

19. The device of claim 16, wherein said computer is operative to register a pattern of light on the photosensitive array and to determine deviations between said registered pattern and a current pattern of light on the photosensitive array.

20. A method of training for dichotic learning, comprising the following steps:

monitoring the accommodation of an eye which is undergoing training;

presenting a reference sound to the ear which is associated with the other eye;

presenting a variable sound to the ear associated with the eye which is undergoing training, said variable sound varying with said accommodation of the eye which is undergoing training; and instructing the patient to make the variable sound match the reference sound.

21. A method of training for dichotic learning, comprising the following steps:

monitoring the accommodation of an eye which is undergoing training;

presenting a reference visual stimulus to the other eye;

presenting a variable visual stimulus to the eye which is undergoing training, said variable visual stimulus varying with said accommodation of the eye which is undergoing training; and instructing the patient to make the variable visual stimulus match the reference visual stimulus.

22. The method of claim 21, further comprising the step of providing, to the ear associated with the eye which is undergoing training, a sound representing the accommodation of the eye which is undergoing training.

23. A method of training a patient to enter the alpha state, comprising the following steps:

monitoring the accommodation of an eye;

presenting the patient with a biofeedback representation of said accommodation;

monitoring the patient's brainwaves;

presenting the patient with a biofeedback representation of said brainwaves; and instructing the patient to maintain said biofeedback representations as instructed.

24. A method of training a patient for enhanced performance, comprising the following steps:

monitoring the position of an eye;

presenting the patient with a biofeedback representation of said position;

monitoring the patient's brainwaves;

presenting the patient with a biofeedback representation of said brainwaves; and instructing the patient to maintain said biofeedback representations as instructed.

25. The method of claim 24, further comprising the step of monitoring an electromyogram of one of the patient's muscles.

* * * * *